United States Patent [19]

Muchel et al.

[11] 4,272,165
[45] Jun. 9, 1981

[54] OPTICAL SYSTEM FOR ILLUMINATING THE GROUND OF THE EYE

[75] Inventors: Franz Muchel, Konigsbronn; Albrecht Vogel, Oberkochen, both of Fed. Rep. of Germany

[73] Assignee: Carl Zeiss-Stiftung, Wuerttenberg, Fed. Rep. of Germany

[21] Appl. No.: 868,460

[22] Filed: Jan. 10, 1978

[30] Foreign Application Priority Data

Jan. 29, 1977 [DE] Fed. Rep. of Germany ....... 2703723

[51] Int. Cl.³ .............................................. A61B 3/10
[52] U.S. Cl. ............................................ 351/13; 351/6
[58] Field of Search .................. 351/6, 13, 16, 14, 32; 350/287, 10, 11, 12

[56] References Cited

U.S. PATENT DOCUMENTS

| 2,107,305 | 2/1938 | Ogle | 351/32 X |
| 3,487,835 | 1/1970 | Koester et al. | 351/16 X |
| 3,524,702 | 8/1970 | Bellows et al. | 351/13 X |
| 3,535,027 | 10/1970 | Littmann et al. | 351/14 |
| 3,572,910 | 3/1971 | Koester | 351/13 |
| 3,600,098 | 8/1971 | Mohrman | 351/6 X |
| 3,880,501 | 4/1975 | Munnerlyn | 351/13 |

Primary Examiner—John K. Corbin
Assistant Examiner—Rodney B. Bovernick
Attorney, Agent, or Firm—Hopgood, Calimafde, Kalil, Blaustein & Lieberman

[57] ABSTRACT

The invention contemplates an improved optical system for illuminating the retina or ground of the eye and having particular application to a hand-held ophthalmoscope. The optical system, thus embodied, permits selective modification of image scale, for a test mark or marks projected in the eye. Two embodiments are disclosed.

4 Claims, 2 Drawing Figures

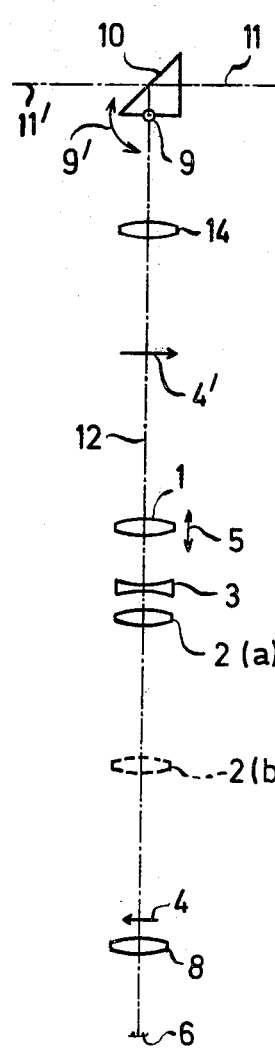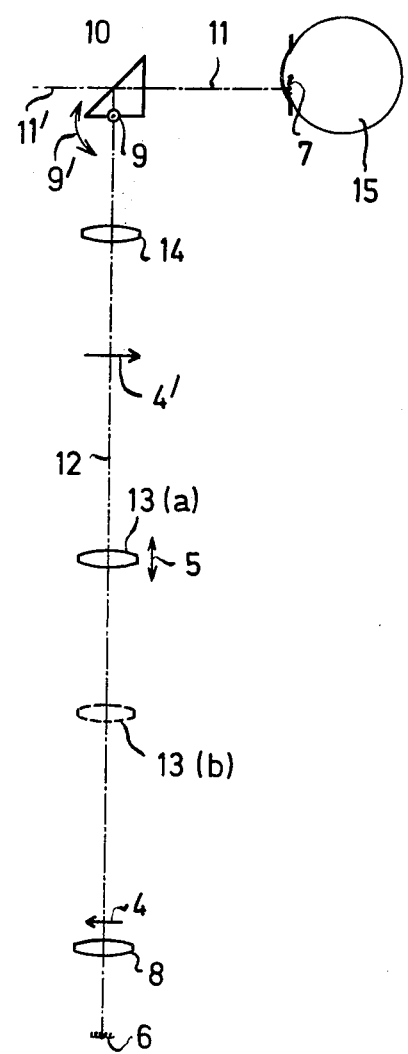

OPTICAL SYSTEM FOR ILLUMINATING THE GROUND OF THE EYE

This invention relates to an optical system for illuminating the ground of the eye and for projecting test marks on it.

Such optical systems are intended for ophthalmoscopes which, on basis of modern methods of ophthalmology, can be used not only for the pure observation of the fundus, but, in addition, also for diagnosis of strabismus, for the treatment of strabismus, for the relative and absolute measurement of pathological changes on the fundus with respect to size and position, and for the quantitative measurement of prominentia, for instance, of the optic disk.

These ophthalmological examinations which go beyond mere observation of the fundus can only be carried out if diagrams or measurement marks are projected onto the ground of the eye of the patient, independently of the ametropia of the patient, in such a manner that the apertures or measurement marks are sharply seen simultaneously during the examination by the doctor and by the patient in accordance with a preselected image scale.

The object of the invention is therefore to provide an optical system which makes it possible, with a selectively variable imaging scale, to focus field diagrams and/or test marks on the ground of the eye. For a given range of defects in sight, the condition should be satisfied that the position of the exit pupil of the optical system shall move only within a range which does not interfere with illumination of the ground of the eye or with the formation of the image of the test marks.

This object is achieved in accordance with the invention by providing a hand-held ophthalmoscope with a light collector bearing a test mark in the path of light between the source of light and the ophthalmological objective, and by providing displaceable optical means within the ophthalmoscope for producing a test-mark image which can be displaced along the optical axis. The range of displacement of such optical means is so selected that the imaging scale, or magnification, can vary from its maximum value $\beta$ to its minimum value $1/\beta$.

In one advantageous embodiment of the invention, the imaging system consists of two displaceable condensing lenses, and a diverging lens which is fixed in position between the condensing lenses. In the ray path as seen from the source of light, both the condensing lenses are arranged in such a way that the one follows after the light collector and the other is followed by the ophthalmological objective, the condensing lens which follows after the light collector and the diverging lens being so dimensioned that together they focus the plane of the test mark at infinity, while the condensing lens which is followed by the ophthalmological objective is so dimensioned that it produces an image within the finite.

It is also possible for those skilled in the art to combine the refractive powers of such a three-element imaging system into a single member which is adapted to be arranged for displacement along the optical axis and with which an image scale ranging between $\beta$ and $1/\beta$ can be obtained for every condition of the eye of the patient.

In order to shift the position of the image of the source of light at right angles to the optical axis, a prism which is swingable about a fulcrum is advantageously arranged in front of the eye of the patient.

The particular advantage obtained with the invention is that the optical system can be provided in a handy instrument which represents a further development of the well-known hand-held ophthalmoscope; thus, in addition to mere observation of the fundus, the new instrument can also be used for the diagnosis and treatment of strabismus and for measurements of pathological changes of the fundus.

One illustrative embodiment of the invention is shown in the drawing and will be described in further detail below. In the drawing:

FIG. 1 is a diagram showing an optical system in accordance with the invention, wherein the imaging system consists of three individual elements; and FIG. 2 is a diagrammatic showing of an optical system in accordance with the invention, wherein the imaging system consists of a group of lenses combined to form a single member.

FIG. 1 depicts part of a hand-held ophthalmoscope incorporating an imaging system of the invention wherein the imaging system utilizes three individual lens elements 1, 2 and 3, on a first axis 12. Other parts of the instrument comprise a light source 6, shown as a coiled filament, a collector lens 8 and an ophthalmological objective 14, all on the axis 12. A prism 10 folds axis 12 substantially 90° to the axis 11 of projection to the image plane 7, within the eye 15 under examination, and it will be understood that the external projection 11' of the axis 11 is schematically suggestive of the viewing system used by the observer who is examining the eye 15.

In its position designated a in FIG. 1, the lens element 2 is in solid lines, and the lens combination 2–3 has the focal length $f_1$; an imaging scale $\beta$ is thus obtained in conjunction with lens element 1, the image of the test mark 4 being formed at 4'. In its position designated b, element 2 is shown in dashed lines, and an imaging scale $1/\beta$ is obtained for the lens combination 2–3 in conjunction with lens element 1. In both positions of element 2, an infinite image distance is obtained for the combination of lens elements 2 and 3. Therefore, by axially displacing lens element 1, as suggested by the arrow 5, it is possible, without impairing the selected scale, to effect a change in the position of the image (4') as it results in accordance with the character of the eye 15 of the patient (defective vision or normal vision). Focal-point positions vary only slightly upon displacement of the lens elements 2 and 1, respectively. Therefore, the position of the image 7 of the light filament 6 can, in cooperation with the ophthalmological objective 14, be maintained relatively constant. The position of the image 7 of the filament represents the exit pupil of the optical system. By swinging the prism 10 about the pivot axis 9, the position of the image 7 of the filament can be moved in a plane perpendicular to the optical axis 11, the latter being 90° away from the optical axis 12; manual means for accomplishing such swinging displacement will be understood to be suggested by the double arrow 9'.

In FIG. 2, the parts which correspond to FIG. 1 bear the same designations. The optical elements 1, 2 and 3 are combined, according to FIG. 2, into a single optical member 13. In the a-designated position of the member 13, there is obtained, for the optical system, an image scale $\beta$; and in the b-designated position of member 13, an image scale of $1/\beta$ is obtained.

What is claimed is:

1. In an optical system for illuminating the ground of a patient's eye and for forming the image of a test mark thereon, in which system a collector and a test mark are provided in the path of light along an optical axis and between a source of light and an opthalmological objective, and in which system an imaging system is displaceably positioned along the optical axis between the test mark and the opthalmological objective, the improvement in which the displaceable imaging system comprises (a) a two-lens system comprising a condensing lens and a diverging lens and forming an image of the test mark at infinity, whereby by displacing the condensing lens along the optical axis, the image scale may be varied, and (b) a further condensing lens arranged in the parallel beam of light behind said two-lens system and so dimensioned that upon its axial displacement a change in the axial position of the image is affected without changing the image scale.

2. The improvement of claim 1, in which said first-mentioned condensing lens and said further condensing lens are independently displaceable, whereby image scale can be varied independently of the instantaneous axial position of the image, and whereby axial position of the image can be varied independently of the instantaneous scale of the image.

3. The improvement of claim 1, further comprising a pivotable prism disposed between the ophthalmological objective and the eye of the patient.

4. In an optical system for illuminating the ground of a patient's eye and for forming the image of a test mark thereon, in which system a collector and a test mark are provided in the path of light along an optical axis and between a source of light and an ophthalmological objective, and in which system an imaging system is displaceably positioned along the optical axis between the test mark and the ophthalmological objective, the improvement in which the displaceable imaging system comprises (a) a multiple-element lens system wherein one of the elements is a condensing lens, said lens system forming an image of the test mark at infinity, whereby, due solely to displacement of said condensing lens along the optical axis, the image scale may be varied without changing the axial position of the image, and (b) a further condensing lens so dimensioned that, due solely to displacement of said further condensing lens, a change in axial position of the image is effected without changing the image scale.

* * * * *